United States Patent [19] [11] 4,334,510
Croset et al. [45] Jun. 15, 1982

[54] ELECTROCHEMICAL SENSOR FOR MEASURING RELATIVE CONCENTRATIONS OF REACTIVE SPECIES IN A FLUID MIXTURE AND A SYSTEM COMPRISING SAID SENSOR, ESPECIALLY FOR REGULATION

[75] Inventors: Michel Croset; Gonzalo Velasco, both of Paris, France

[73] Assignee: Thomson-CSF, Paris, France

[21] Appl. No.: 95,308

[22] Filed: Nov. 19, 1979

[30] Foreign Application Priority Data

Nov. 21, 1978 [FR] France .................................. 78 32764

[51] Int. Cl.$^3$ ...................... F02M 7/00; G01N 27/46
[52] U.S. Cl. ................................. 123/440; 204/195 S
[58] Field of Search ............................. 123/440, 489; 204/195 S

[56] References Cited

U.S. PATENT DOCUMENTS 3,787,308 1/1974 Malaspina et al. ............... 204/195 P
3,907,657 9/1975 Heijne et al. ..................... 123/536 X
3,952,710 4/1976 Kawarada et al. ................. 123/489
4,101,403 7/1978 Kita et al. .......................... 204/195 S
4,117,815 10/1978 Ikeura ............................... 123/489 X
4,132,615 1/1979 Linder et al. ..................... 204/195 S
4,140,611 2/1979 Yaegashi et al. ................. 204/195 S
4,227,496 10/1980 Martel ................................... 123/440
4,231,334 11/1980 Peter ..................................... 123/440
4,264,425 4/1981 Kimura et al. ................... 123/489 X

FOREIGN PATENT DOCUMENTS

2711880 9/1978 Fed. Rep. of Germany ... 204/195 S

Primary Examiner—Tony M. Argenbright
Attorney, Agent, or Firm—Cushman, Darby & Cushman

[57] ABSTRACT

An electrochemical sensor for measuring relative concentrations of reactive species in a fluid mixture with a first catalytic enclosure for bringing the fluid mixture into thermodynamic equilibrium, and a second enclosure having an electrochemical cell which is responsive to an excess of one of the reactive species with respect to stoichiometry of the reaction. Additional structure for selectively impeding the transfer of species of the fluid mixture to be analyzed are located upstream of or combined with the first enclosure and serve to modify the ratio of relative concentrations of the reactive species of the fluid mixture in predetermined proportions.

13 Claims, 16 Drawing Figures

ELECTROCHEMICAL SENSOR FOR MEASURING RELATIVE CONCENTRATIONS OF REACTIVE SPECIES IN A FLUID MIXTURE AND A SYSTEM COMPRISING SAID SENSOR, ESPECIALLY FOR REGULATION

This invention relates to electrochemical sensors for measuring the relative concentrations of reactive species in a fluid mixture and in particular in a gas.

Figure 1:
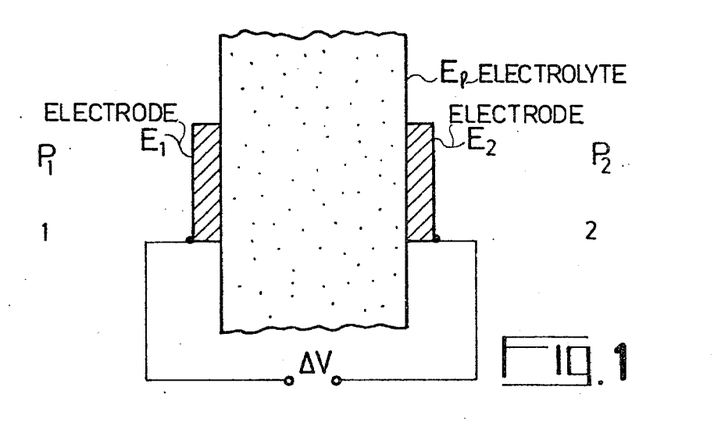
FIG. 1 illustrates diagrammatically the operation of the measuring cell employed in electrochemical sensors for measuring relative concentrations of reactive species in a fluid mixture.

One of the well-known families of sensors for the measurement of partial gas pressures operates on the principle of a concentration cell. By way of example, the gas mixture to be analyzed consists of oxygen and carbon monoxide. As shown in FIG. 1 of the accompanying drawings, said mixture is present within a compartment 2 and separated from a reference medium 1 by the wall of a solid electrolyte $E_I$, each face of which is adapted to carry an electrode designated respectively by the references $E_2$-$E_1$. As is well known, the equations governing these sensors are:

at the electrode/electrolyte interfaces:

(1)

the voltage then developed between the electrodes is given by the Nernst law:

$$\Delta v = \frac{RT}{4F} \ln \frac{P_1}{P_2} \quad (2)$$

with
R: ideal gas constant = 8.314 J(mole. °K.).
F: Faraday number = 96490
T: absolute temperature in degrees Kelvin
$P_1$ and $P_2$: partial pressures of media 1 and 2 within compartments 1 and 2
if the mixture within compartment 2 is at equilibrium, the function of the electrode $E_2$ is limited to the oxidation-reduction reaction:

(3)

if the electrode is also a catalyst, the following reaction takes place:

$$2Co + O_2 \rightleftharpoons 2Co_2 \quad (4)$$

and finally, if the combustion is complete until a reversible thermodynamic equilibrium is attained, the following relation is established:

(5)

where K(T) is a coefficient of equilibrium which depends on the temperature and $|CO|$, $|O^2|^{\frac{1}{2}}$, $|CO^2|$ are the partial pressures of carbon monoxide, oxygen and carbon dioxide gas.

The invention relates to sensors of this type, namely in which the electrodes or other means placed upstream of the measuring electrochemical cell are catalysts, with the result that the gas mixture to be analyzed attains the thermodynamic equilibrium at least at the level of the electrode-electrolyte interface.

Sensors of this type are commonly employed for regulating internal combustion engines and in particular for regulating the admission of the air-fuel mixture at the level of the carburetor. In this case the sensor is placed in the exhaust system and analyzes the relative concentration of oxygen-carbon monoxide species contained in the gas. The sensor must accordingly be adapted to certain characteristics which are specific to this application. The exhaust gas will in fact arrive in the form of periodic bursts in synchronism with the reciprocating motion of the different pistons. These difficulties are solved by withdrawing samples of gas to be analyzed and admitting said samples alone into the sensor in which they will be brought to a state of thermodynamic equilibrium. If they are withdrawn at sufficiently short time intervals, these so-called "test samples" tend towards a continuous analysis although the sensor in fact operates in a dynamic regime. In order to achieve this result, means for selectively retarding the gas which flows through the sensor and limiting gaseous exchange between the external medium and the interior of said sensor are usually placed upstream of this latter. By analogy with the laws governing electric circuits, the retarding means just mentioned will be designated hereinafter as "transfer-impeding" means. A number of different solutions proposed up to the present time are based on two approaches: in accordance with the first approach, the gas mixture to be analyzed passes into the sensor through one or a number of calibrated orifices; in accordance with the second approach, the gas mixture passes through a porous solid material.

It has been observed in the past that experimental data and in particular the measurement of the stoichiometric ratio of a gas mixture did not always corroborate the real value. Apart from the fact that catalysis is not always complete in certain catalyst structures, it should be noted that the transfer-impeding means in accordance with the second approach as defined in the foregoing are not neutral with respect to the different species constituting the mixture.

In particular, in the case of a mixture of two species such as oxygen and carbon monoxide, for example, one of the species may diffuse more rapidly than the other within the porous material under consideration. In other words, a different mixture composition within the porous material and subsequently at the level of the measuring electrode $E_2$ may correspond to a given mixture composition at the inlet of the sensor.

The invention proposes a structure of sensors which makes profitable use of this physical phenomenon by integrating in the sensor means for selectively impeding the transfer of species of a fluid mixture and especially a gas mixture, said transfer-impeding means being associated with catalytic means for bringing the gas mixture into thermodynamic equilibrium prior to analysis. Sensors of this type serve to measure the apparent concentration of the species of a gas mixture, that is to say the concentration existing at the level of the measuring electrode $E_2$.

The invention is therefore directed to an electrochemical sensor for measuring relative concentrations of reactive species contained in a fluid mixture, in which provision is made for first means comprising a catalyst whereby the fluid mixture to be analyzed is brought into thermodynamic equilibrium and for second means in cascade comprising an electrochemical cell which is sensitive to an excess of one of the reactive species with respect to the stoichiometry of the reaction and for additional means located upstream of the second means and forming means for selectively impeding the transfer of species of the fluid mixture to be analyzed, the ratio of relative concentrations of the reactive species contained in the fluid mixture to be analyzed being modified in predetermined proportions by said transfer-impeding means.

The invention is further directed to the application of the aforementioned sensors to regulation of admission of the air-fuel mixture into combustion engines.

Further distinctive features will become apparent from the following description which will serve to gain a more complete understanding of the invention, reference being made to the accompanying drawings in which.

FIG. 1 illustrates diagrammatically the operation of a measuring cell of the concentration cell type. The measuring cell comprises a solid electrolyte $E_l$ and two electrodes $E_1$ and $E_2$. The gas contained within compartment 1 is at a reference partial pressure $P_1$ and can be the atmosphere in the case in which the gas mixture to be analyzed is a mixture of oxygen and carbon monoxide. For this application, the electrodes can be of platinum and the electrolyte can be of lime-stabilized zirconium. This electrolyte is an ionic conductor of oxygen. The electrodes produce or collect the electrons required for the electrochemical reactions which take place at the interfaces (1). The oxygen of the gas mixture to be analyzed which is present within the compartment 2 is at a partial pressure $P_2$. In the state of equilibrium corresponding to equalization of the electrochemical potential of the oxygen within the three media, the voltage $\Delta V$ developed across the terminals of the electrodes is produced by the Nernst law mentioned earlier (2) and detected by any suitable measuring circuit.

Figure 2:
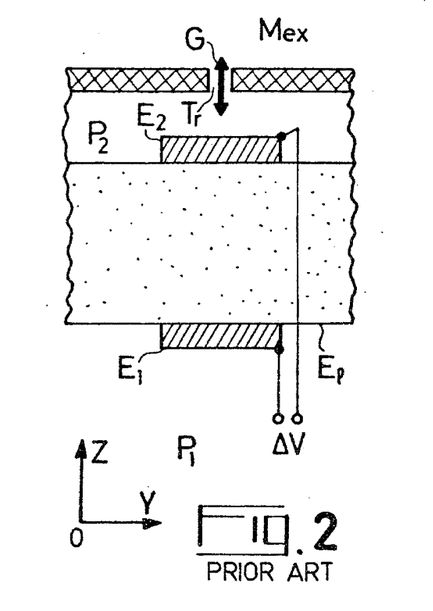
FIG. 2 illustrates one example of construction of an electrochemical sensor according to a first approach.
Figure 3:
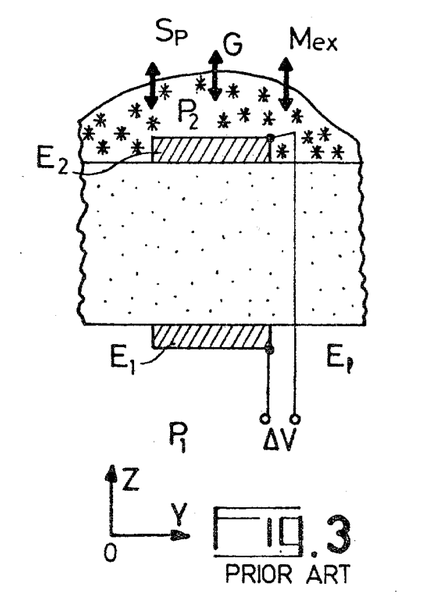
FIG. 3 illustrates one example of construction of an electrochemical sensor according to a second approach.
Figure 4:
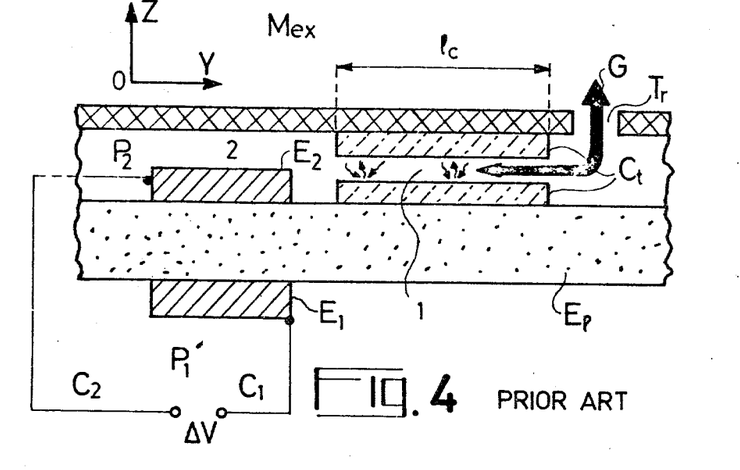
FIG. 4 illustrates an improvement of the sensor of FIG. 2.
Figure 5:
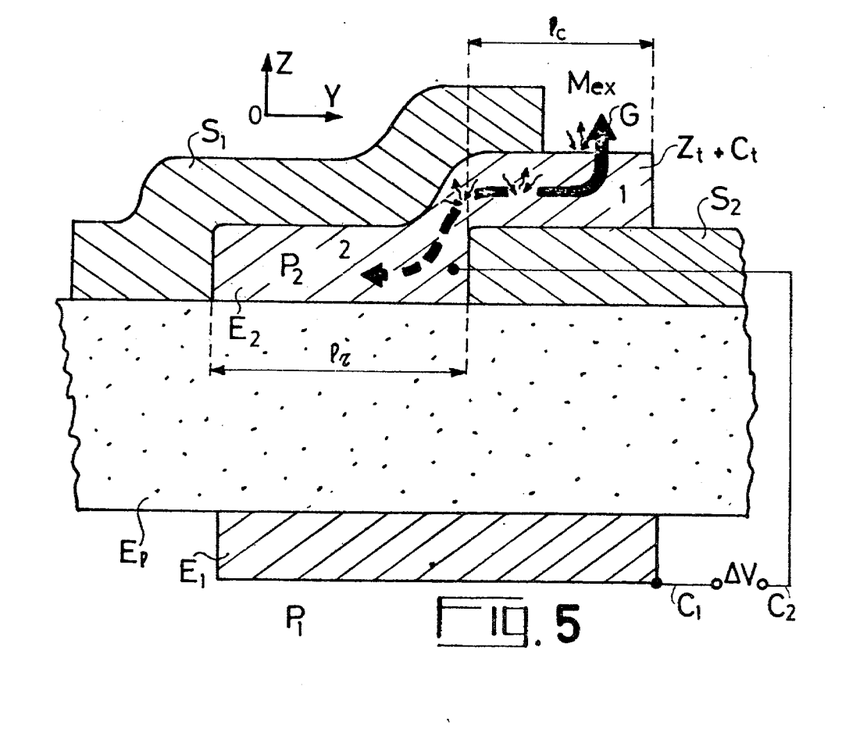
FIG. 5 illustrates an improvement of the sensor of FIG. 3 in which the structure can also be employed for producing an alternative form of sensor in accordance with the invention.

FIGS. 2 and 3 illustrate examples of sensors constructed respectively in accordance with the first approach and second approach. In other words, said sensors are provided with transfer-impeding devices of the type comprising a calibrated orifice $T_r$ in FIG. 2 or of the type consisting of the porous solid material $S_p$ shown in FIG. 3. The measuring cell "$E_1$-$E_l$-$E_2$" of FIG. 1 is again present in these two cases. The gas G to be analyzed circulates in the external medium Mex. In these two cases also, catalysis of the gas mixture admitted into the sensor takes place during traversal in the direction of the thickness or in other words in the direction OZ of the electrode $E_2$ which is formed of catalytic material such as platinum, for example. This method is not satisfactory since provision must be made for an electrode of sufficient thickness to ensure catalysis. This has the disadvantage on the one hand of increasing the cost price of the electrode which is formed of precious metal and on the other hand of reducing the dynamic response of the cell. In consequence, structures providing improvements in the sensors which are constructed in accordance with these two approaches have been proposed. These improvements introduce catalytic means which are dissociated from the measuring electrode. The gas mixture to be analyzed passes through an enclosure upstream of the measuring cell in which catalysis takes place. This catalyst $C_t$ according to the first approach lines an enclosure over a distance $l_c$ (zone 1) into which the gas is admitted through a calibrated orifice $T_r$ as illustrated in FIG. 4 or fills this enclosure as illustrated in FIG. 5. In both cases the layers of catalyst are of small thickness and only that surface of the catalyst which is in contact with the gas to be analyzed has a large area. In FIG. 5, the solid material (which may or may not be porous) of zone 1 acts as a catalyst $C_t$ and as a transfer-impeding element $Z_t$. The sensor of FIG. 5 will be described in detail hereinafter since its structure can be employed in an alternative form of sensor in accordance with the invention.

Figure 6:
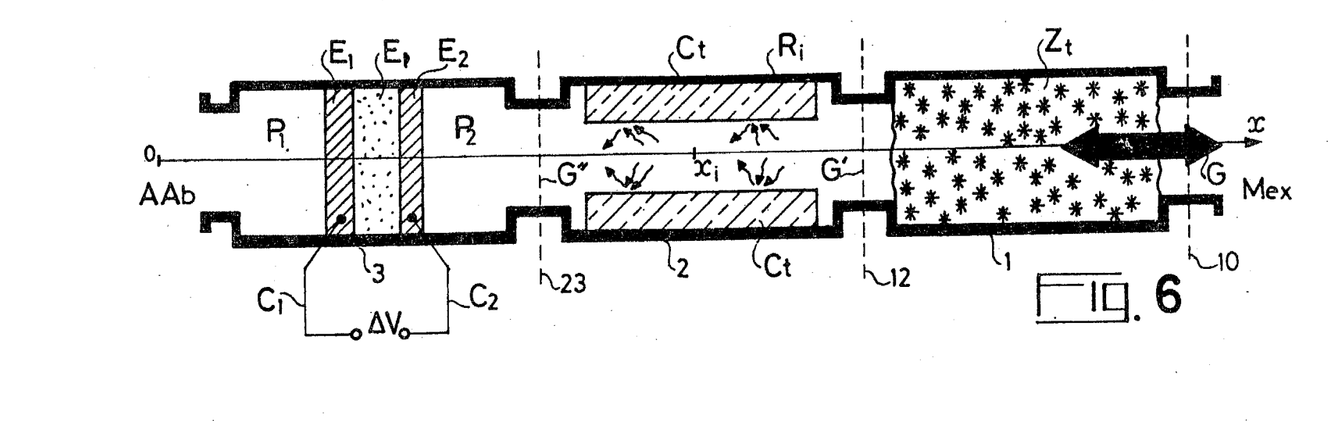
FIG. 6 illustrates the theoretical structure of a sensor according to the invention.
Figure 7:
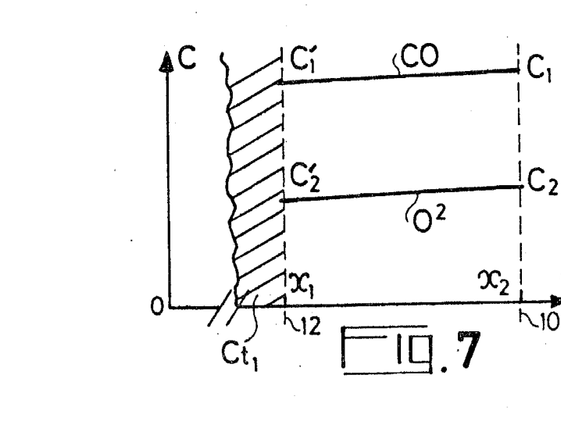
FIGS. 7 and 8 are explanatory diagrams of two modes of operation of the sensor of FIG. 6.
Figure 8:
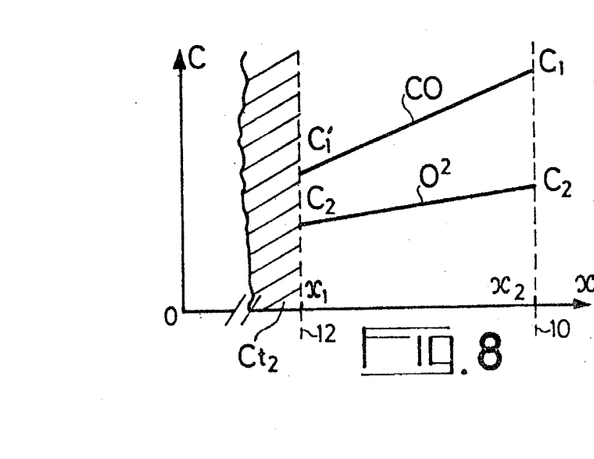

The operation of an electrochemical sensor according to the invention will now be explained with reference to FIGS. 6 to 8. FIG. 6 shows a theoretical model of a sensor of this type. For the sake of convenience, it will be assumed in the following explanation that said sensor is of revolution about an axis OX. This sensor is divided into three zones, namely a zone 1 designated as a "transfer impedance" $Z_t$ which communicates with the external medium Mex containing the gas G to be analyzed, a zone 2 containing the catalyst $C_t$ and a zone 3 containing an electrochemical measuring cell "$E_2$-$E_l$-$E_1$". The interface between the external medium and the zone 1 is represented by the index 10; the interface between zone 1 and zone 2 is represented by the index 12 and the interface between zone 2 and zone 3 is represented by the index 23. It is assumed that the interface 10 does not provide any transfer impedance of the type comprising a calibrated orifice $T_r$ (as in FIGS. 2 and 4). Zone 1 contains a solid material in which the gas G is intended to diffuse and then to arrive at the interface 12 in the form G'. It is assumed that the gas G is formed of carbon monoxide and of oxygen. Said gas is then subjected to a catalytic process within the enclosure 2 in which it reacts with the catalyst $C_t$ at each point of abscissa $x_i$ so as to produce the reaction $R_i$ in accordance with the equation given earlier (4). The gas G'' at the exit of the enclosure 2 is then analyzed by the cell "$E_2$-$E_t$-$E_1$" and a potential difference $\Delta V$ is developed across the terminals of the electrodes $C_1$, $C_2$ in accordance with the Nernst law (2). This potential difference is not directly representative of the concentrations $C_1/C_2$ respectively of carbon monoxide CO and of oxygen $O_2$ at the interface 10 but of $c_1''$ and $c_2''$ at the interface 23 (namely of the medium $P_2$). The medium $P_1$ is a reference medium which can be the ambient air AAb, for example.

In order to explain the transfer process between the interfaces 10 and 23, two cases must be considered:

It will first be supposed that the transfer impedance is of low value (in other words that diffusion takes place at a high speed) and that the catalytic process is insufficient or slow. Catalysis results in consumption of the type $CO + \frac{1}{2}O_2 \rightleftharpoons CO_2$ according to the reaction already set forth (1). Since the diffusion is rapid, the two species (CO and $O_2$) are delivered at each instant to the enclosure 2 in a sufficient quantity to ensure that there is no appreciable difference in composition between G and G''. As a consequence, the concentrations $C_1'$ and $C_2'$ remain practically unchanged with respect to $C_1$ and $C_2$ on the interface 10. This case is illustrated in FIG. 7. The interfaces 10 and 12 are represented at $x_1$ and $x_2$ on the axis Ox and the concentrations $C_1$, $C_2$ and $C_1'$ and $C_2'$ are plotted as ordinates. The hatched zone $Ct_1$ represents the catalytic enclosure 2.

It will now be supposed that the rate of catalytic reaction (that is to say the consumption of the two species in accordance with equation (2)) is high compared with the rate of renewal of at least one of the species (namely its diffusion current) by reason of a high transfer impedance $Z_t$ with respect to said species. In this case and as illustrated in FIG. 8, the absolute and relative concentrations of carbon monoxide and of oxygen of the mixture G' at the interface 12 (and also of G'' at the interface 23) are different from those of the mixture G at the interface 10.

The diffusion current $G_i$ of a species i is given by Fick's law:

$$J_i = -D_i \frac{\partial C}{\partial x} \quad (6)$$

where
$D_i$ is the diffusion constant in the medium constituting the impedance $Z_t$;
x is a predetermined point of Ox;
C is the concentration at said predetermined point of Ox.

If $D_1$ is the diffusion constant of the carbon monoxide and $D_2$ is the diffusion constant of oxygen at all points $x_i$ of the axis Ox in zone 1 and in particular at the interface 12, the ratio of concentrations: $C_1/C_2$ is dependent only on the ratio: $D_1/D_2$ and on the distance covered along the axis Ox. In the case of gaseous diffusion, this ratio is in turn governed by the relation:

$$\frac{D_1}{D_2} = K(T) \sqrt{\frac{M_1}{M_2}} \quad (7)$$

where
$M_1$ and $M_2$ are the molecular masses of the species 1 and 2 and
K(T) is a temperature-dependent coefficient.

In the case of two given species of a gas mixture, the ratio of concentrations $C_1/C_2$ can therefore undergo a progressive variation in only one direction.

Figure 9:
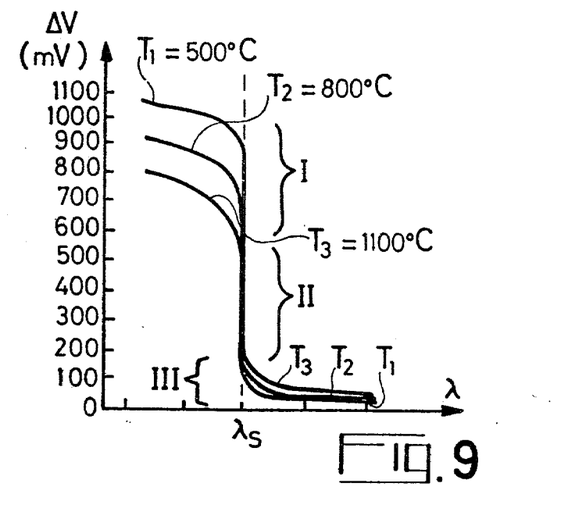
FIG. 9 is a set of response curves of an ideal sensor, said curves being represented as temperature parameters.

Reference will now be made to FIG. 9 which represents a family of response curves of an ideal sensor, namely without any transfer impedance. A sensor as illustrated in FIG. 4 has a response curve which is little different from the theoretical response curve. This arises from the fact that the transfer impedance $T_r$ is practically neutral with respect to the different species of the gas mixture G to be analyzed and consequently does not affect the relative concentrations. The abscissa $\lambda$ represents the ratio of concentrations of the reactive gases at the inlet of the sensor and normed at the stoichiometric concentration $\lambda_s$. In the case of the mixture $CO + O_2$, we have:

$$\lambda = \frac{\left[\frac{|O_2|}{|CO|}\right] \text{real ratio}}{\left[\frac{|O_2|}{|CO|}\right] \text{stoichiometric ratio}} \quad (8)$$

In region II, the curves practically coincide, which is not the case in regions I and III. This is due to the effect of temperature by virtue of equations (2) and (5). There have been shown three curves: in which $T_1 = 500°$ C., $T_2 = 800°$ C. and $T_3 = 1100°$ C.

Figure 10:
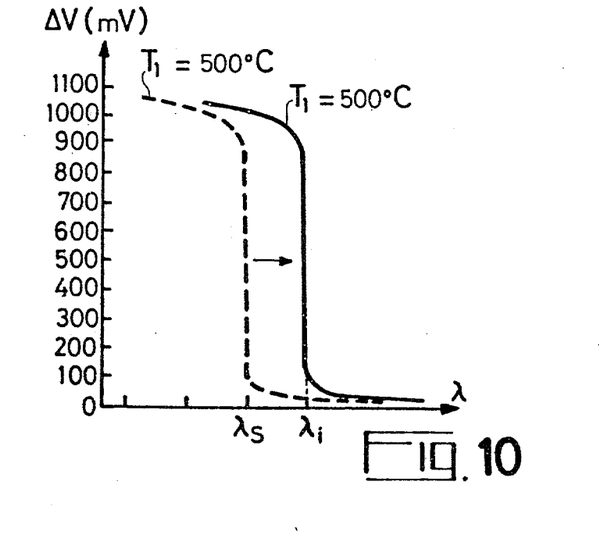
FIG. 10 illustrates a response curve of a sensor in accordance with the invention.

FIG. 10 represents the response curve of a sensor in accordance with the invention (at a given temperature $T_1 = 500°$ C.). It is apparent that the point of abscissa $\lambda_i$ is displaced with respect to the point of abscissa $\lambda_s$. It has just been shown with reference to FIGS. 6 and 8 that the mixture G'' is different from the mixture G which is present at the inlet of the sensor, namely the mixture to be analyzed which circulates within the external medium Mex. The point $\lambda_i$ is therefore representative of the apparent stoichiometric ratio of the gas to be analyzed. It is immediately apparent that, by providing a predetermined impedance at the manufacturing stage (for example by adjusting the length of the zone 1), steps can be taken to ensure that the inflexion of the curve corresponds to a given composition of the mixture at the sensor inlet. In fact, if $\lambda_i$ corresponds to the measured stoichiometric ratio at the level of the electrode $E_2$ (medium $P_2$) it is possible to predict either by calculation of the diffusion parameters or by experimentation the composition of the mixture G at the sensor inlet when detecting relative concentrations corresponding to stoichiometry of the mixture at the level of the electrochemical cell (medium $P_2$).

Figure 11:
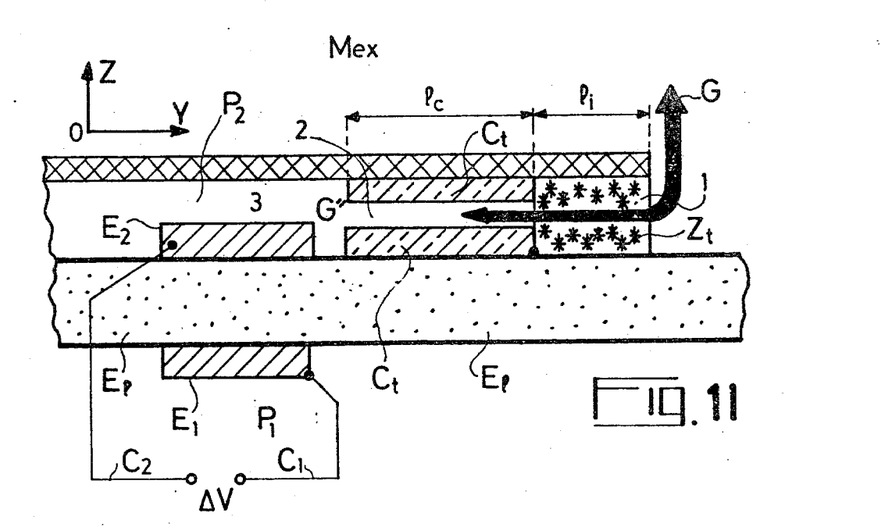
FIGS. 11 and 12 are sensors constructed in accordance with the invention.

FIG. 11 shows an example of construction of an electrochemical sensor in accordance with the invention. The general structure of FIG. 4 is again shown except for the zone 1 of FIG. 11 which is filled with porous material forming the impedance $Z_t$ over a distance $l_i$. Provision is then made over a distance $l_c$ for the zone 2 lined with catalyst $C_t$ and for the zone 3 containing the electrochemical measuring cell "$E_2$-$E_t$-$E_1$". The potential difference $\Delta V$ is collected at the terminals of the electrodes $E_1$, $E_2$ via the leads $C_1$, $C_2$. In the case of a sensor of this type, the response curve obtained is of the type illustrated in FIG. 10. By modifying the value $l_i$, it is possible to "adjust" the point $\lambda_i$ which will be detected subsequently by means of a threshold logic circuit, for example.

The transfer impedance $Z_t$ can have a base of zirconia, alumina or of any other refractory cement. Typical values of $l_i$ are within the range of a few microns to a few hundred microns, depending on the porosity. A relative displacement in the direction of increase of $\lambda_i$ of the order of 15% with respect to $\lambda_s$ can readily be achieved by employing alumina as transfer impedance in the event that the sensor employed analyzes the composition of a mixture of carbon monoxide and oxygen. The structure of a sensor in accordance with the invention is not limited to that shown in FIG. 11. Other sensor structures of the prior art can be converted in the same manner by inserting therein an impedance $Z_t$ consisting of suitable porous material.

Figure 12:
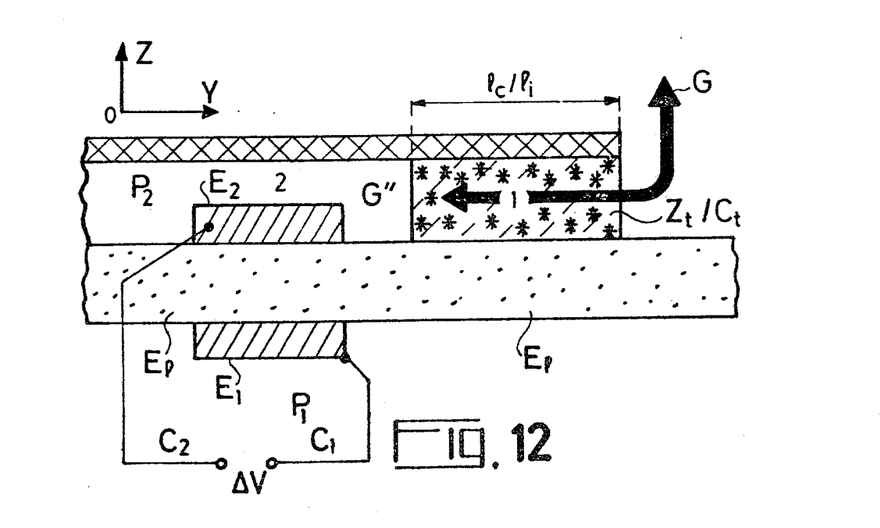

FIG. 12 illustrates an alternative embodiment of a sensor which is similar to the design of FIG. 11 described earlier. The difference between this embodiment and the preceding lies in the fact that the catalyst $C_t$ and the transfer impedance $Z_t$ are formed within the same porous material which has intrinsic catalytic properties or is well charged with a catalyst. It will be seen hereinafter that the operation of this sensor is similar to the operation which has just been explained. The sensor structure of FIG. 5 is another variant of this type.

It should nevertheless be noted that, in the case of a given gas composition such as oxygen and carbon monoxide, for example, the ratio $C_1/C_2$ can be varied only in one direction in agreement with equations (6) and (7). Other sensor structures which make it possible to overcome this limitation will be described hereinafter.

The distinctive feature of the sensors shown in FIG. 12 and also in FIG. 5 mentioned earlier lies in the fact that a catalyst $C_t$ and an impedance $Z_t$ are intimately associated. This process can be referred to as diffusion with catalytic reaction. In fact, the zone 1 performs these two functions. It will be necessary at this stage to distinguish two cases:

It will first be assumed that the material which fills the zone 2 is a porous substance charged with catalyst as in FIG. 12. A gaseous diffusion mode is thus maintained. The laws (6) and (7) set forth earlier remain valid. In order to produce a significant effect, the consumption by catalysis at all points of $l_i$ of the species of the mixture must be faster than the supply of these species by diffusion current.

Another case to be studied is the behavior of the sensor if the material is a permeable solid substance and a catalyst. This is the case of the sensor shown in FIG. 5 and accordingly corresponds to a solid diffusion mode. The process in this case is much more complex. The diffusion at each point essentially depends on the reactivity between a given species and the solid material. In the case of a given fluid mixture, experience shows that certain catalytic substances cause the ratio $C_1/C_2$ to vary in one direction and other catalytic substances produce a variation in the opposite direction.

Figure 13:
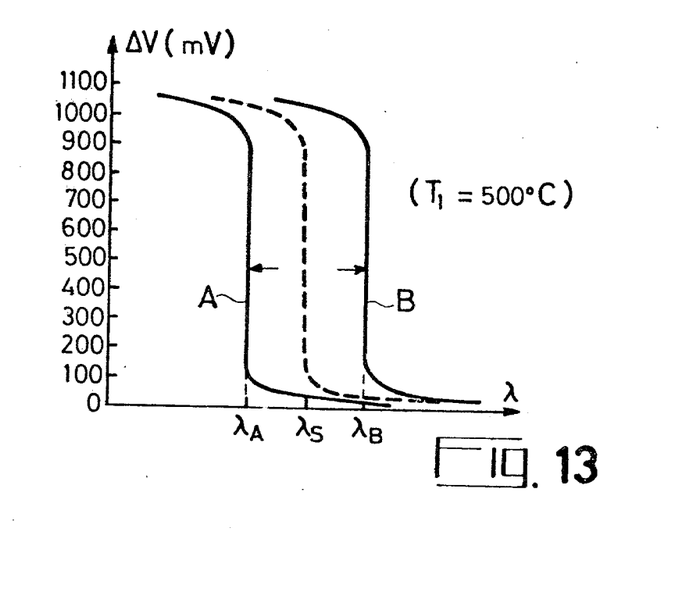
FIG. 13 illustrates the response curves of two sensors constructed in accordance with the invention by utilizing the alternative embodiment of FIG. 5.

By way of a non-limitative example in the case of the mixture of oxygen and carbon monoxide, the diagram of FIG. 13 gives the response curves of two sensors in which the catalytic substances are selected so as to ensure that the point of apparent stoichiometry $\lambda_i$ is "advanced" in the case of the first sensor (curve A) and "retarded" in the case of the second sensor (curve B).

The structure of FIG. 5 is therefore suitable for the fabrication of a sensor in accordance with the invention. It is only necessary to adjust the distance $l_c$ during fabrication and to choose a suitable material for the formation of the zone 1. The electrode $E_2$ can be constituted by the same material. The materials $S_1$ and $S_2$ are electrically insulating and leak-tight materials. The other sensor components mentioned earlier, namely $E_2$, $E_I$, $E_1$, $P_1$, are again present in this structure.

This sensor has the advantage of flexibility of adjustment in regard to the ratio designated as the apparent stoichiometric ratio $\lambda_i$ since it is possible to cause the ratio $C_1/C_2$ of the mixture G to vary in either increasing or decreasing directions.

It is particularly advantageous to apply the sensors of the invention to regulation of admission of the air-fuel mixture into an internal combustion engine.

Figure 14:
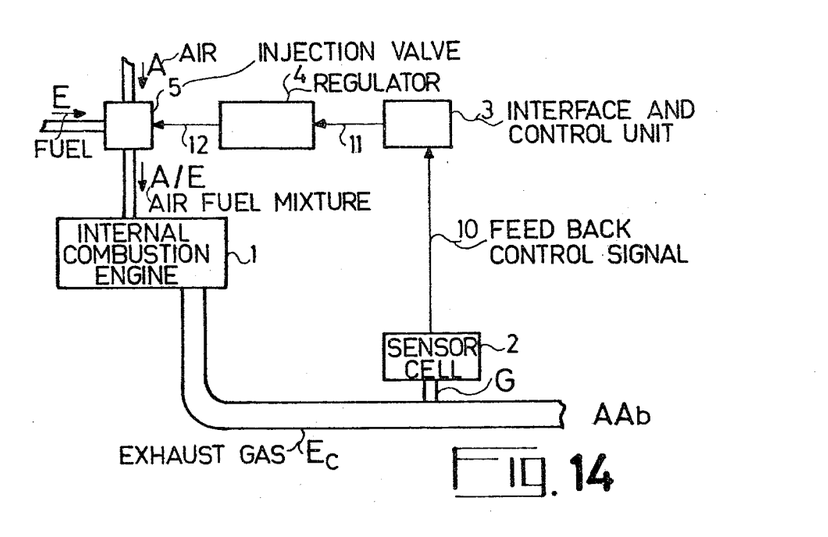
FIGS. 14 and 15 illustrate two modes of application of sensors in accordance with the invention to regulation of admission of the air-fuel mixture into an internal combustion engine.

FIG. 14 is a block diagram showing the regulation of the air-fuel mixture in an internal combustion engine 1. The engine 1 comprises an air intake A and a fuel intake E, said air and fuel being mixed within a unit 5. Said unit can be a carburetor of the float-chamber type, an injection device or any other similar device. The mixture is fed to the engine 1 through the duct A/E. The unit 5 is under the control of a regulating unit 4. The connection 12 can be a mechanical coupling shaft, for example. The burnt gases are then discharged into the atmosphere AAb through an exhaust system $E_c$. A sensor 2 in accordance with the invention is placed in the flow path and communicates with the exhaust gas through the duct designated by the reference G. In practice, the sensor is inserted in the exhaust pipe and maintained in position by any suitable fastening means. The signal developed between the electrodes $E_2$, $E_1$ of the electrochemical measuring cell is transmitted to a control unit by means of the electrical connections 10. The control unit must have a high input impedance in order to limit the current which flows through the electrochemical measuring cell. By making use of a threshold logic circuit, for example, the control unit must be capable of detecting the inflexion of the curve $\Delta V$ about $80_s$ (FIG. 10) or $\lambda_A$ or $\lambda_B$ (FIG. 13) and the output of said unit controls the regulator 4 via the connection 11. In the case under consideration, the reference medium $P_1$ of the measuring cell is ambient air AAb.

This method of regulation differs from the prior art only in the use of a sensor in accordance with the invention which makes it possible to detect a relatively displaced value and not a fixed and single value ($\lambda_s$ or a very closely related value), said relatively displaced value being pre-established at the fabrication stage by means of a judicious choice of the transfer impedance $Z_t$ which is included in the sensor. This detected value makes it possible to establish an optimized running speed of the engine in order to conform, for example to antipollution standards or in order to obtain higher efficiency.

Figure 15:
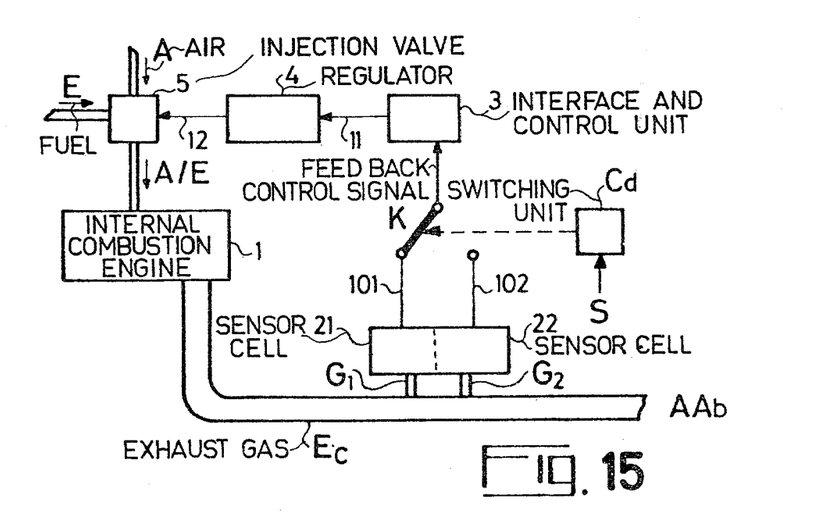

FIG. 15 is an improvement in the method of regulation hereinabove described. The behavior of an internal combustion engine in the cold state at the moment of starting is in fact very different from the hot-state behavior after a variable operating time which depends on the inherent characteristics of the engine. It is therefore particularly advantageous to provide a plurality of reference points which define a plurality of ranges of regulation of the air-fuel ratio. In addition to the elements which are common to FIG. 14, FIG. 15 shows two sensors 21 and 22 provided with different transfer impedances. These impedances can be selected from a standardized range of impedances. This would be the case of equipment directed to the automobile industry for use by the general public. In the case of applications to professional equipment, the transfer impedance $Z_t$ can also be adjusted individually. A switch K operated by a control unit $C_d$ directs either the output signals 101 of the sensor 21 or the output signals 102 of the sensor 22 towards the unit 3 which is described with reference to FIG. 14. The control unit $C_d$ can be actuated either by hand or automatically. In FIG. 15, a signal S delivered by a probe such as a temperature probe, for example, initiates changeover of the switch K from 101 to 102 by means of the control unit $C_d$. It is possible to employ an amplifier followed by a contact relay K. Anyone versed in the art can readily find other satisfactory design solutions. By way of non-limitative example, it is possible to employ two sensors having respectively the response curves A and B of FIG. 13. The two detected points are therefore $\lambda_A$ and $\lambda_B$ which correspond to two gas mixtures of different composition within the exhaust pipe and, by feedback effect, to two air-fuel ratios of the mixture which is admitted into the engine 1.

Although a regulating system which makes use of two sensors has been described with reference to FIG. 15, this number can be increased at will without thereby departing from the scope of the invention. Furthermore, the field of application of electrochemical sensors in accordance with the invention is not limited to regulation of admission of the air-fuel mixture into an internal combustion engine.

The sensors in accordance with the invention can also be applied to regulation of production of a fluid mixture at the stoichiometric value of the mixture (if the sensor detects $\lambda_s$) or in the vicinity of this value and in a predetermined proportion (if the sensor detects $\lambda_s \times x\%$, where x depends on the transfer impedance $Z_t$ of the sensor).

Figure 16:
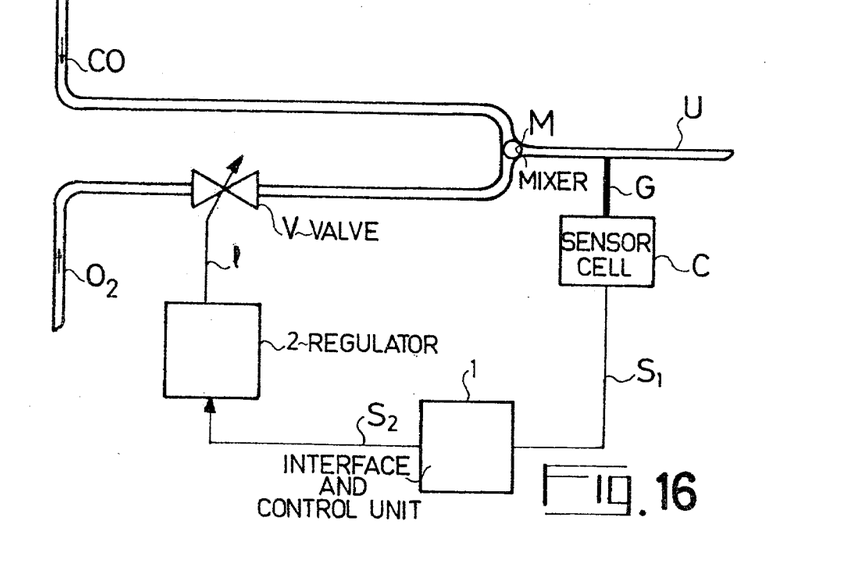
FIG. 16 illustrates the application of sensors in accordance with the invention to regulation of the production of a fluid mixture of two species in a ratio which is close to stoichiometry.

FIG. 16 is a schematic illustration of the application just mentioned. Two gaseous species, namely oxygen and carbon monoxide, must be mixed in a stoichiometric ratio ($\lambda_s$) or in a ratio ($\lambda_i$) which differs therefrom by a predetermined value (x; with $\lambda_i = \lambda_s \pm x\%$). These two species are supplied through separate pipes CO and $O_2$ so as to be mixed and delivered to a utilization unit (not shown) via the pipe U. A sensor C in accordance with the invention analyzes the mixture which is circulated within the pipe U via the gaseous exchange orifice G as defined earlier. The output signal $S_1$ of the sensor C which detects inflexion of the voltage response curve about $\lambda_s$ or more generally about $\lambda_i$ is transmitted to a shaping circuit 1 which can be constituted by an amplifier and a threshhold detection logic circuit. The output of this circuit controls a regulator 2 for producing action on a valve V which is inserted in the pipe $O_2$. The connection 1 can consist of a mechanical coupling shaft, for example. The valve V therefore regulates the oxygen flow rate so as to supply to a utilization unit a gas mixture having a predetermined relative concentration of two species. The choice of a transfer impedance of given nature and of given value wholly defines the composition of the fluid mixture which circulates within the pipe U. The mixing process takes place within the mixture M. As in the case of FIG. 15, a plurality of different transfer-impedance sensors can be employed and each sensor diffuses a value $x_i\%$.

Other fluid mixtures can be regulated in the same manner. There can thus be mentioned by way of non-limitative example the regulation of fuel for rocket propulsion units (oxygen-hydrogen mixture) or of water gas (mixture of carbon monoxide and water).

What is claimed is:

1. An electrochemical sensor for measuring relative concentrations of reactive species contained in a fluid mixture, comprising:
    first catalyst means for bringing the fluid mixture to be analyzed into thermodynamic equilibrium;
    second means in cascade with said first means including an electrochemical cell which is sensitive to an excess of one of the reactive species with respect to the stoichiometry of the reaction; and
    additional means located upstream of said second means for selectively impeding the transfer of species of the fluid mixture to be analyzed, the ratio of relative concentrations of the reactive species contained in the fluid mixture to be analyzed being modified in predetermined proportions by said transfer-impeding means to obtain a substantial and predetermined shift of the stoichiometric concentration measured at said cell.

2. A sensor according to claim 1, wherein said transfer-impeding means consist of an inert porous body through which the fluid mixture to be analyzed passes along a predetermined length of said body.

3. A sensor according to claim 1, wherein said catalyst means and said additional means are combined so as to form a unitary structure.

4. A sensor according to claim 3, wherein said catalyst means combined with said transfer-impeding means consists of a catalytic porous body through which the fluid mixture to be analyzed passes along a predetermined length of said body.

5. A sensor according to claim 3, wherein said catalyst means combined with said transfer-impeding means consists of a catalytic solid body, said body being permeable to the species of the fluid mixture which passes through said body along a predetermined length.

6. A sensor comprising transfer-impeding means according to claim 2, wherein the direction of variation of the ratio of relative concentrations of two of the species of a fluid mixture during the passage of said mixture through said transfer-impeding means is wholly determined by the nature of the species which are present in the fluid mixture, the amplitude of said variation of the ratio of said relative concentrations being solely dependent on said predetermined length of said porous body which constitutes said transfer-impeding means and on the ratio of the square roots of the molecular masses of said two species.

7. A sensor comprising transfer-impeding means according to claim 5, wherein the direction of variation of the ratio of relative concentrations of two of the species of a fluid mixture during the passage of said mixture through said transfer-impeding means is determined by the nature of the catalytic solid body which constitutes said transfer-impeding means, the amplitude of the variation of the ratio of said relative concentrations being dependent on said predetermined length of said catalytic solid body.

8. A system for regulating the air-fuel mixture of an internal combustion engine by electrochemical analysis of the exhaust gases composed of species to be analyzed, comprising a device for proportioning said air-fuel mixture, a control intake for said device, and a measuring unit comprising at least one electrochemical sensor for measuring relative concentrations of reactive species contained in a fluid mixture, comprising:
    first catalyst means for bringing the fluid mixture to be analyzed into thermodynamic equilibrium;

second means in cascade with said first means including an electrochemical cell which is sensitive to an excess of one of the reactive species with respect to the stoichiometry of the reaction; and additional means located upstream of said second means for selectively impeding the transfer of species of the fluid mixture to be analyzed, the ratio of relative concentrations of the reactive species contained in the fluid mixture to be analyzed being modified in predetermined proportions by said transfer-impeding means to obtain a substantial and predetermined shift of the stoichiometric concentration measured at said cell, the output signals of said unit being transmitted to said control intake of said proportioning device.

9. A system according to claim 8, wherein said measuring unit comprises a plurality of said sensors and having different values of transfer impedance for defining a corresponding number of air-fuel proportions.

10. A system for regulating the proportions of a fluid mixture comprising two reactive species, wherein said system is provided for each species with a separate admission pipe and each pipe is fitted with an adjustable valve, a mixer for said species which is supplied through said pipes and a regulating loop comprising a control unit for actuating said adjustable valve, said control unit being provided with a control intake and a measuring unit connected to said control intake and comprising at least one electrochemical sensor for measuring relative concentrations of reactive species contained in a fluid mixture comprising:

first catalyst means for bringing the fluid mixture to be analyzed into thermodynamic equilibrium;

second means in cascade with said first means including an electrochemical cell which is sensitive to an excess of one of the reactive species with respect to the stoichiometry of the reaction; and additional means located upstream of said second means for selectively impeding the transfer of species of the fluid mixture to be analyzed, the ratio of relative concentrations of the reactive species contained in the fluid mixture to be analyzed being modified in predetermined proportions by said transfer-impeding means to obtain a substantial and predetermined shift of the stoichiometric concentration measured at said cell.

11. A method of manufacturing an electrochemical sensor for measuring relative concentrations of reactive species contained in a fluid mixture of the type having an electrochemical cell which is sensitive to an excess of one of the reactive species with respect to the stoichiometry of the reaction, a catalyst in cascade with the cell for bringing the mixture to be analyzed into thermodynamic equilibrium and a fluid impedance upstream of said cell for impeding the transfer of species of the mixture to be analyzed comprising the steps of:

selecting a desired shift of the stoichiometric concentration measured at the cell and forming said impedance to selectively impedance transfer of species to modify the ratio and relative concentrations of the reactive species in predetermined proportions to thereby shift said stoichiometric concentration measured at the cell.

12. A method as in claim 11 wherein said step of forming includes forming a catalytic body constituting said impedance of a length so as to cause said desired shift.

13. A method as in claim 11 including the further step of selecting said impedance so as to cause modification in a desired direction.

* * * * *